(12) United States Patent
Jennewine (10) Patent No.: US 8,353,881 B2
(45) Date of Patent: Jan. 15, 2013

(54) INFUSION SETS FOR THE DELIVERY OF A THERAPEUTIC SUBSTANCE TO A PATIENT (75) Inventor: R. Curtis Jennewine, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1053 days.

(21) Appl. No.: 11/322,166

(22) Filed: Dec. 28, 2005

(65) Prior Publication Data
US 2009/0105658 A1 Apr. 23, 2009

(51) Int. Cl.
*A61M 5/32* (2006.01)
*A61M 25/00* (2006.01)

(52) U.S. Cl. .................. 604/265; 604/272; 604/523

(58) Field of Classification Search ............ 604/272, 604/265, 523
See application file for complete search history.

(56) References Cited

U.S. PATENT DOCUMENTS

| | | | |
|---|---|---|---|
| 2,755,036 A | 7/1956 | Mikko | |
| 3,923,060 A | 12/1975 | Ellinwood, Jr. | |
| 4,003,379 A | 1/1977 | Ellinwood, Jr. | |
| 4,601,707 A | 7/1986 | Albisser et al. | |
| 4,685,903 A | 8/1987 | Cable et al. | |
| 4,886,505 A | 12/1989 | Haynes et al. | |
| 5,019,096 A | 5/1991 | Fox, Jr. et al. | |
| 5,097,834 A | 3/1992 | Skrabal | |
| 5,236,143 A | 8/1993 | Dragon | |
| 5,237,993 A | 8/1993 | Skrabal | |
| 5,266,359 A * | 11/1993 | Spielvogel | 427/388.4 |
| 5,344,411 A * | 9/1994 | Domb et al. | 604/265 |
| 5,437,656 A | 8/1995 | Shikani et al. | |
| 5,451,424 A * | 9/1995 | Solomon et al. | 427/2.1 |
| 5,569,186 A | 10/1996 | Lord et al. | |
| 5,593,852 A | 1/1997 | Heller et al. | |
| 5,599,321 A | 2/1997 | Conway et al. | |
| 5,662,904 A * | 9/1997 | Ferguson et al. | 424/130.1 |
| 5,925,021 A | 7/1999 | Castellano et al. | |
| 6,134,461 A | 10/2000 | Say et al. | |
| 6,175,752 B1 | 1/2001 | Say et al. | |
| 6,254,586 B1 | 7/2001 | Mann et al. | |
| 6,284,478 B1 | 9/2001 | Heller et al. | |
| 6,427,088 B1 | 7/2002 | Bowman, IV et al. | |
| 6,471,689 B1 | 10/2002 | Joseph et al. | |
| 6,482,156 B2 | 11/2002 | Iliff | |
| 6,554,798 B1 | 4/2003 | Mann et al. | |
| 6,558,321 B1 | 5/2003 | Burd et al. | |
| 6,562,001 B2 | 5/2003 | Lebel et al. | |
| 6,564,105 B2 | 5/2003 | Starkweather et al. | |
| 6,571,128 B2 | 5/2003 | Lebel et al. | |
| 6,577,899 B2 | 6/2003 | Lebel et al. | |
| 6,585,644 B2 | 7/2003 | Lebel et al. | |
| 6,635,014 B2 | 10/2003 | Starkweather et al. | |
| 6,648,821 B2 | 11/2003 | Lebel et al. | |
| 6,659,948 B2 | 12/2003 | Lebel et al. | |
| 6,668,196 B1 | 12/2003 | Villegas et al. | |
| 6,687,546 B2 | 2/2004 | Lebel et al. | |

(Continued)

FOREIGN PATENT DOCUMENTS
WO WO-01/52935 7/2001
(Continued)

*Primary Examiner* — Victoria P Shumate
(74) *Attorney, Agent, or Firm* — Jackson & Co., LLP (57) ABSTRACT

Devices and methods for delivering a therapeutic substance to a patient are provided. Embodiments include infusion sets that include an active agent. Also provided are systems and kits.

35 Claims, 3 Drawing Sheets

U.S. PATENT DOCUMENTS

| | | |
|---|---|---|
| 6,694,191 B2 | 2/2004 | Starkweather et al. |
| 6,702,857 B2 | 3/2004 | Brauker et al. |
| 6,733,446 B2 | 5/2004 | Lebel et al. |
| 6,736,797 B1 | 5/2004 | Larsen et al. |
| 6,740,075 B2 | 5/2004 | Lebel et al. |
| 6,741,877 B1 | 5/2004 | Shults et al. |
| 6,744,350 B2 | 6/2004 | Blomquist |
| 6,758,810 B2 | 7/2004 | Lebel et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,852,104 B2 | 2/2005 | Blomquist |
| 6,862,465 B2 | 3/2005 | Shults et al. |
| 6,873,268 B2 | 3/2005 | Lebel et al. |
| 6,887,270 B2 | 5/2005 | Miller et al. |
| 6,902,207 B2 | 6/2005 | Lickliter |
| 6,931,327 B2 | 8/2005 | Goode, Jr. et al. |
| 6,946,446 B2 | 9/2005 | Ma et al. |
| 6,950,708 B2 | 9/2005 | Bowman IV et al. |
| 6,958,705 B2 | 10/2005 | Lebel et al. |
| 6,974,437 B2 | 12/2005 | Lebel et al. |
| 7,024,245 B2 | 4/2006 | Lebel et al. |
| 7,052,251 B2 | 5/2006 | Nason et al. |
| 7,074,307 B2 | 7/2006 | Simpson et al. |
| 7,079,977 B2 | 7/2006 | Osorio et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,155,112 B2 | 12/2006 | Uno et al. |
| 7,171,274 B2 | 1/2007 | Starkweather et al. |
| 7,192,450 B2 | 3/2007 | Brauker et al. |
| 7,226,978 B2 | 6/2007 | Tapsak et al. |
| 7,267,665 B2 | 9/2007 | Steil et al. |
| 7,276,029 B2 | 10/2007 | Goode, Jr. et al. |
| 7,310,544 B2 | 12/2007 | Brister et al. |
| 2002/0016719 A1 | 2/2002 | Nemeth et al. |
| 2002/0107476 A1 | 8/2002 | Mann et al. |
| 2002/0147135 A1 | 10/2002 | Schnell |
| 2003/0023317 A1 | 1/2003 | Brauker et al. |
| 2003/0032874 A1 | 2/2003 | Rhodes et al. |
| 2003/0065308 A1 | 4/2003 | Lebel et al. |
| 2003/0069541 A1* | 4/2003 | Gillis et al. ............... 604/164.01 |
| 2003/0122021 A1 | 7/2003 | McConnell et al. |
| 2003/0144362 A1* | 7/2003 | Utterberg et al. ............. 514/724 |
| 2003/0175323 A1 | 9/2003 | Utterberg et al. |
| 2003/0176933 A1 | 9/2003 | Lebel et al. |
| 2003/0212379 A1 | 11/2003 | Bylund et al. |
| 2003/0217966 A1 | 11/2003 | Tapsak et al. |
| 2004/0011671 A1 | 1/2004 | Shults et al. |
| 2004/0045879 A1 | 3/2004 | Shults et al. |
| 2004/0122530 A1 | 6/2004 | Hansen et al. |
| 2004/0186362 A1 | 9/2004 | Brauker et al. |
| 2004/0193090 A1 | 9/2004 | Lebel et al. |
| 2004/0199059 A1 | 10/2004 | Brauker et al. |
| 2004/0210180 A1* | 10/2004 | Altman ........................ 604/4.01 |
| 2004/0210208 A1* | 10/2004 | Paul et al. ..................... 604/500 |
| 2004/0225338 A1 | 11/2004 | Lebel et al. |
| 2005/0004439 A1 | 1/2005 | Shin et al. |
| 2005/0010269 A1 | 1/2005 | Lebel et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0065464 A1 | 3/2005 | Talbot et al. |
| 2005/0090607 A1 | 4/2005 | Tapsak et al. |
| 2005/0112169 A1 | 5/2005 | Brauker et al. |
| 2005/0143635 A1 | 6/2005 | Kamath et al. |
| 2005/0176136 A1 | 8/2005 | Burd et al. |
| 2005/0181010 A1 | 8/2005 | Hunter et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0245795 A1 | 11/2005 | Goode, Jr. et al. |
| 2005/0245799 A1 | 11/2005 | Brauker et al. |
| 2005/0261667 A1* | 11/2005 | Crank et al. .................. 604/529 |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0095020 A1* | 5/2006 | Casas et al. ................. 604/890.1 |
| 2006/0173406 A1 | 8/2006 | Hayes et al. |
| 2006/0173444 A1 | 8/2006 | Choy et al. |
| 2006/0222566 A1 | 10/2006 | Brauker et al. |
| 2006/0224141 A1 | 10/2006 | Rush et al. |
| 2007/0163880 A1 | 7/2007 | Woo et al. |
| 2007/0191702 A1 | 8/2007 | Yodfat et al. |
| 2007/0203966 A1 | 8/2007 | Brauker et al. |
| 2007/0213657 A1 | 9/2007 | Jennewine et al. |
| 2007/0235331 A1 | 10/2007 | Simpson et al. |
| 2007/0299409 A1* | 12/2007 | Whitbourne et al. ......... 604/264 |
| 2008/0004515 A1 | 1/2008 | Jennewine et al. |
| 2008/0004601 A1 | 1/2008 | Jennewine et al. |
| 2008/0021666 A1 | 1/2008 | Goode, Jr. et al. |

FOREIGN PATENT DOCUMENTS

| | | |
|---|---|---|
| WO | WO-01/54753 | 8/2001 |
| WO | WO-2006/037109 | 4/2006 |
| WO | WO-2007/101260 | 9/2007 |
| WO | WO-2008/003003 | 1/2008 |
| WO | WO-2008/005780 | 1/2008 |

* cited by examiner

INFUSION SETS FOR THE DELIVERY OF A THERAPEUTIC SUBSTANCE TO A PATIENT

BACKGROUND OF THE INVENTION

Delivery devices for administering a therapeutic agent to a patient are available in a variety of configurations. In one such configuration, a delivery device includes an infusion set to deliver therapeutic substances to a patient transcutaneously, e.g., to a target subcutaneous site. Such infusion sets generally include a cannula that provides a transcutaneous pathway through which a therapeutic substance may be administered to a patient. The cannula typically includes an insertion needle for providing an opening in the patient's skin through to place the cannula transcutaneously; thereafter the needle may be removed leaving the cannula transcutaneously positioned. The therapeutic substance desired to be delivered to the patient via the cannula is typically retained in a therapeutic agent source that is connected to the cannula via flexible tubing.

These and other types of infusion sets may be intended to remain in a transcutaneous position, and to deliver a therapeutic substance to a patient, over a period of time. For example, insulin delivery devices are often intended to infuse insulin to a patient for a period of time, e.g., about three days, without removal.

Because infusion sets may be used for multiple days, the risk of infection at the infusion site exists. This risk is of constant concern to users of such infusion sets and healthcare professionals. The risk of infection increases as the time period of use increases, thereby limiting the duration of use of the infusion set and requiring frequent replacements.

Accordingly, as infusion sets for the delivery of therapeutic substances to patients continues to be of importance in health management, there continues to be an interest in devices and methods that decrease the risk of infection associated with infusion sets. Of particular interest are infusion devices for the delivery of therapeutic substances to patients that decrease the risk of infection and increase the period of time an infusion set may be left in place to deliver a therapeutic substance to a patient.

SUMMARY OF THE INVENTION

The subject invention provides devices and methods for delivering a therapeutic substance to a patient that has minimal risk of infection. Embodiments of the subject invention include extended wear infusion sets and methods of delivering therapeutic substances to patients over extended periods of time, e.g., 3 days or more, e.g., 5 days or more, without replacement of the infusion set during the period.

Embodiments of the subject invention include infusion sets that include an active agent such as an antimicrobial agent and/or anti-scarring agent. In certain embodiments, the active agent may be a time-release formulation.

In certain embodiments, one or more active agents may be included to maintain or increase skin elasticity or turgor around the infusion site, and/or to minimize allergic reaction of the skin around the cannula or skin sensitivity.

Also provided are systems and kits.

BRIEF DESCRIPTION OF THE DRAWINGS

To facilitate understanding, identical reference numerals may be used, where practical, to designate the same elements which are common to different figures. The figures shown herein are not necessarily drawn to scale, with some components and features being exaggerated for clarity.

DEFINITIONS

Throughout the present application, unless a contrary intention appears, the following terms refer to the indicated characteristics.

When one item is indicated as being "remote" from another, this is referenced that the two items are at least in different buildings, and may be at least one mile, ten miles, or at least one hundred miles apart. When different items are indicated as being "local" to each other they are not remote from one another (for example, they can be in the same building or the same room of a building).

"Communicating", "transmitting" and the like, of information reference conveying data representing information as electrical or optical signals over a suitable communication channel (for example, a private or public network, wired, optical fiber, wireless radio or satellite, or otherwise). Any communication or transmission can be between devices which are local or remote from one another.

"Forwarding" an item refers to any means of getting that item from one location to the next, whether by physically transporting that item or using other known methods (where that is possible) and includes, at least in the case of data, physically transporting a medium, carrying the data or communicating the data over a communication channel (including electrical, optical, or wireless).

"Receiving" something means it is obtained by any possible means, such as delivery of a physical item. When information is received it may be obtained as data as a result of a transmission (such as by electrical or optical signals over any communication channel of a type mentioned herein), or it may be obtained as electrical or optical signals from reading some other medium (such as a magnetic, optical, or solid state storage device) carrying the information. However, when information is received from a communication, it is received as a result of a transmission of that information from elsewhere (local or remote).

When two items are "associated" with one another they are provided in such a way that it is apparent that one is related to the other such as where one references the other.

A "computer", "processor" or "processing unit" are used interchangeably and each references any hardware or hardware/software combination which can control components as required to execute recited steps. For example a computer, processor, or processor unit includes a general purpose digital microprocessor suitably programmed to perform all of the steps required of it, or any hardware or hardware/software combination which will perform those or equivalent steps.

Programming may be accomplished, for example, from a computer readable medium carrying necessary program code (such as a portable storage medium) or by communication from a remote location (such as through a communication channel).

A "memory" or "memory unit" refers to any device which can store information for retrieval as signals by a processor, and may include magnetic or optical devices (such as a hard disk, floppy disk, CD, or DVD), or solid state memory devices (such as volatile or non-volatile RAM). A memory or memory unit may have more than one physical memory device of the same or different types (for example, a memory may have multiple memory devices such as multiple hard drives or multiple solid state memory devices or some combination of hard drives and solid state memory devices).

"Reading" signal data from a sensor refers to the detection of the signal data (such as by a detector or meter) from the sensor. This data may be saved in a memory (whether for relatively short or longer terms).

It will also be appreciated that throughout the present application, that words such as "cover", "base" "front", "back", "top", "upper", and "lower" are used in a relative sense only.

"May" refers to optionally.

When two or more items (for example, elements or processes) are referenced by an alternative "or", this indicates that either could be present separately or any combination of them could be present together except where the presence of one necessarily excludes the other or others.

Any recited method can be carried out in the order of events recited or in any other order which is logically possible. Reference to a singular item, includes the possibility that there are plural of the same item present.

DETAILED DESCRIPTION OF EMBODIMENTS OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

As summarized above, the subject invention generally relates to infusion sets of therapeutic substance delivery devices. The infusion sets of the invention include an active agent, wherein many embodiments the active agent includes an antimicrobial agent and/or anti-scarring agent. "Antimicrobial agent" is meant broadly to include any substance of natural, synthetic or semi-synthetic origin known or to be discovered, or combination of substances, that kills or at least inhibits the growth of microbes such as one or more of bacteria, fungi, viruses, and parasites. "Anti-scarring agent" is meant broadly to include any substance of natural, synthetic or semi-synthetic origin known or to be discovered, or combination of substances, that eliminates or at least reduces the production of excessive fibrous (scar) tissue. "Active agent" is used herein to refer to antimicrobial and/or anti-scarring agent(s) and/or any other agent included to provide desired infusion set properties. The subject invention is primarily described herein with respect to insulin delivery for exemplary purposes only, where such description is in no way intended to limit the scope of the invention. The subject invention may find use in the intraperitoneal delivery of insulin.

In that at least a portion of the subject infusion sets includes active agent means that at least some active agent permeates, adheres to, is integrated into, or otherwise becomes associated with one or more of the components of the infusion sets (or other associated component). Thus, as described in greater detail below, active agent may be largely associated with a surface of an infusion set, as in a coating, may penetrate within or between the material of an infusion set, may be covalently or ionically bound to an infusion set, etc. The nature of the association between active agent and the infusion set may depend on the particular agent used, the type and structure of the infusion set being treated, etc.

As described above, in many embodiments the active agent is one or more antimicrobial agents and/or one or more anti-scarring agents. Other active agents may be used in addition to or instead of one or more antimicrobial agents and/or one or more anti-scarring agents. Examples of active agents include, but are not limited to: antibacterial agents (e.g., penicillin, mupirocin, erthromycin, polymyxin, silver sulfadiazine, cephalosporins, bacitracin, tetracycline, doxycycline, gentamycin, quinolines, neomycin, clindamycin, kanamycin, metronidazole, and the like); antiseptic agents (e.g., iodine, Povidine-iodine, benzalkonium chloride, benzoic acid, chlorhexidine, nitrofurazone, benzoyl peroxide, hydrogen peroxide, hexachlorophene, phenol, resorcinol, cetylpyridinium chloride, and the like); antipathogenic polypeptides; antifungal agents (e.g., nystatin, ciclopirox, chloroxylenol, triacetin, sulconazole, undecylenic acid, tolnaftate, miconizole, clotrimazole, oxiconazole, griseofulvin, econazole, ketoconazole, and amphotericin B and the like); antiviral agents (e.g., acyclovir, ribarivin, interferons, and the like); anti-scarring agents (e.g., a cell cycle inhibitor, and the like); anti-inflammatory agents (e.g., triamcilolone, betamethasone, dexamethasone, hydrocortisone, and prednisone; antiparasitic agent such as quinacrine, chloroquine, vidarbine, and the like); analgesic agents (e.g., salicylic acid, acetaminophen, ibuprofen, naproxen, piroxicam, flurbiprofen, morphine, and the like); local anesthetics (e.g., lidocaine, bupivacaine, benzocaine, and the like); immunogens (vaccines, and the like); steroidal and non-steroidal anti-inflammatory drugs and/or peptides, and any combinations thereof. In certain embodiments an antimicrobial agent that is employed includes nitrofurazone, iodine, silver compounds (for example, silver nitrate, silver sulfadiazine, and the like), macrolide compounds (e.g., as described in U.S. Pat. No. 6,946, 446), zinc compounds (for example, zinc oxide, and the like), and combinations thereof.

In certain embodiments, active agent may be combined with one or more other components. For example, active agent may be formulated into preparations for use, e.g., for applying to an infusion set, by dissolving, suspending or emulsifying active agent in an aqueous or nonaqueous solvent, with conventional additives such as solubilizers, isotonic agents, suspending agents, emulsifying agents, stabilizers, preservatives, and the like. These preparations are sterile and generally free of undesirable matter.

In certain embodiments, active agent may be combined with a penetration enhancer to optimize local active agent delivery into and through the skin (Ghosh, T. K. et al. (1993), Pharm. Tech. 17(3):72-98; Ghosh, T. K. et al. (1993), Pharm. Tech. 17(4): 62-89; Ghosh, T. K. et al. (1993), Pharm. Tech. 17(5):68-76). The penetration enhancer may be selected to have one or more of the following properties: pharmacologically inert, non-toxic, and non-allergenic, have rapid and reversible onset of action, and be compatible with the therapeutic substance to be delivered by the infusion set.

Exemplary penetration enhancers include, but are not limited to, ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); N-methyl pyrrolidone, and the like.

Embodiments of the subject infusion sets are extended wear infusion sets in that decreased risk of infection and/or scarring and/or other adverse or otherwise undesirable effects of use, due to the active agent properties of the infusion sets of the subject invention, enables the infusion sets to be maintained in a transcutaneous position for an extended period of time, e.g., 3 days or more, e.g., 5 days or more, e.g., 7 days or more. In certain embodiments, the useful duration period is extended and the frequency of replacement is reduced as compared to conventional infusion sets in which it is recommended that a patient frequently replace a given infusion set such as every few days.

The subject infusion sets may be used to infuse any therapeutic fluid. In many embodiments, and herein further described for exemplary purposes only, the active-agent infusion sets are used to infuse insulin and are part of an insulin pump. In certain embodiments, the subject invention is employed to deliver insulin in a continuous or programmable dosage to a patient.

Figure 1:
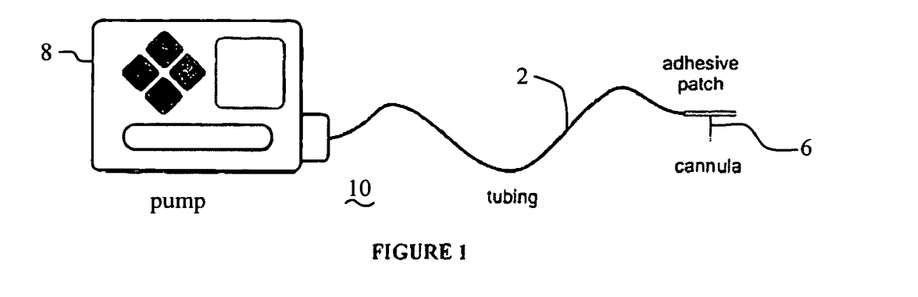
FIG. 1 shows an exemplary embodiment of a therapeutic substance delivery device that includes an active agent, according to the invention.
Figure 2:
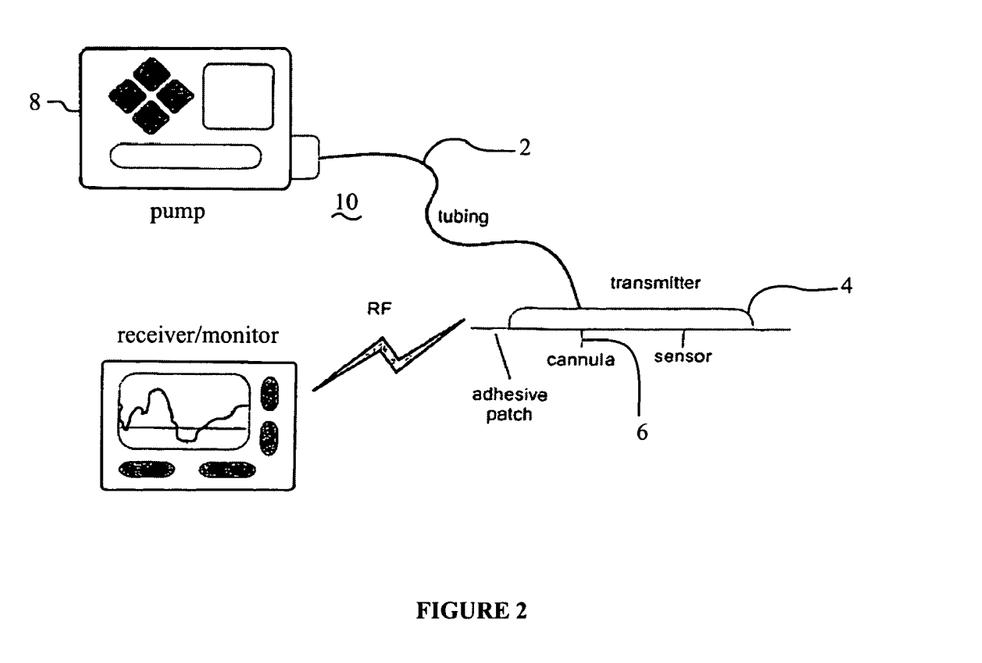
FIG. 2 shows an exemplary embodiment of another therapeutic substance delivery device that includes an integrated analyte monitoring system.

FIGS. 1 and 2 show exemplary embodiments of active-agent including-devices 10 for delivery of a therapeutic substance to a patient. Device 10 includes an infusion set of tubing 2 in fluid communication with a cannula 6. In certain embodiments, tubing may not be included so that the infusion set may include cannula 6, and may or may not have one or more other components described herein, but may not include tubing. In further describing the invention, an infusion set is described primarily as including both tubing 2 and a cannula 6 for exemplary purposes only, where such description is in no way intended to limit the scope of the invention.

In the embodiment of FIG. 2, the cannula 6 is integrated with an analyte sensing device in that cannula 6 is incorporated in the housing of the transmitter and/or securement element 4. The sensor monitor may include a separate user interface from device 10 or the user interface may be the same. Accordingly, in such embodiments a user need only to wear a single securement element 4, on the patient's body, rather than having to wear one for the sensor and a separate securement element 4 for the cannula 6.

The cannula 6 and the tubing 2 each include a wall defining an interior lumen and an exterior surface. The tubing 2 and cannula 6 may be fabricated from durable, non-toxic, biocompatible materials that are compatible with the therapeutic substance to be delivered and which are typically able to withstand sterilization protocols. For example, cannula 6 and/or tubing 2 may be made of a metal and/or polymeric material that is relatively soft and biologically compatible such as, but not limited to, stainless steel, high or low density polyethylene, polypropylene, Nylon, polyurethane, polyimides, silicone, polyvinyl chloride, polysulfones, polyfluorocarbons, polyethylene terephthalate, copolymers; or polyester elastomers, and mixtures of the above.

As noted above, a needle (not shown) is often included to facilitate the transcutaneous placement of the cannula 6. An infusion set securement element 4 may be included to secure the infusion set to the skin of the patient during use, and usually is low profile so as to be easily concealable under an article of clothing. Element 4 may include adhesive on a side thereof. In certain embodiments, element 4 is an adhesive patch such as that may include a backing with an adhesive surface. Materials used as the backing layer may include, but are not limited to, sheets or films of polyolefins, polyesters, polyurethanes, polyvinyl alcohols, polyvinyl chlorides, polyvinylidene chloride, polyamides, ethylene-vinyl acetate copolymer (EVA), ethylene-ethylacrylate copolymer (EEA), vinyl acetate-vinyl chloride copolymer, cellulose acetate, ethyl cellulose, metal vapour deposited films or sheets thereof, rubber sheets or films, expanded synthetic resin sheets or films, non-woven fabrics, fabrics, knitted fabrics, paper and foils, and the like. Other backings will be readily apparent to those skilled in the art.

"Infusion set" is meant to include any structure or combination of structures that is used to deliver a therapeutic agent from a source to a patient, where infusion sets include a cannula 6 with or without optional tubing 2 and with or without optional securement element 4 or other structure for maintaining the cannula 6 in place and with or without an optional cannula insertion element.

The infusion set is connectable to housing 8, e.g., via a releasable or non-releasable coupling, together providing therapeutic substance delivery device 10. Housing 8 retains the therapeutic substance source, e.g., an insulin container, in an interior space. In certain embodiments, the therapeutic substance source may be easily replaceable in the housing 8. Containers suitable for holding therapeutic substances such as insulin include instruments of containment that may be used to deliver, place, attach, and/or insert the therapeutic substance into the housing 8 for administration of the medication to a patient and include, but are not limited to, vials, ampules, tubes, capsules, bottles, syringes and bags.

Housing 8 may be an implantable or external pump, e.g., an insulin pump. Where it is an external pump, it may be configured to be attachable to the patient or article of clothing of the patient, e.g., wearable on a belt (e.g., in the manner of a pager or cellular telephone or the like) or other article of clothing. The housing 8 includes a processor to pump insulin from the reservoir that contains the insulin to the patient, and may include a processor for determining an appropriate dose of insulin based on certain inputs such as glucose levels, food intake, insulin levels, etc. Accordingly, the pump may be adapted to controllably deliver insulin to the patient under the direction of a processor and/or the patient or healthcare worker. Housing 8 may also include a glucose meter for determining the level of glucose from a test strip or continuous glucose sensor. For example, in certain embodiments a test strip port may be included for receiving a test strip. A test strip may be used to confirm the glucose level prior to insulin delivery, e.g., to confirm a previously obtained glucose level as a safeguard measure. In certain embodiments, the pump may be adapted to automatically receive, e.g., wirelessly or using a physical connection, glucose information from a glucose sensor, a portion of which sensor may be transcutaneously positioned in the patient. The pump may receive glucose information from any suitable source, wirelessly or using a physical connection.

Active agent may be included with any component of device 10, and is typically included at least in a patient-contacting component. For example, tubing 2 and/or cannula 6 and/or element 4 and/or the needle of the infusion set may include active agent.

The active agent-containing component(s) may be the infusion set in certain embodiments, or may be a structure that is positionable near an infusion site. That is, in certain embodiments active agent may not be carried by an infusion set, but rather may be otherwise applied at or substantially near the infusion site.

Active agent employed in the subject invention may be delivered transdermally, by a topical route, formulated as applicator sticks, solutions, suspensions, emulsions, gels, creams, ointments, pastes, jellies, paints, powders, and aerosols. Such formulations may be included in adhesive patch 4, other transdermal patch or other part of an infusion set, or may be a separate component. Embodiments may include an active agent in the form of a discrete patch or film or plaster or the like adapted to remain in intimate contact with the epidermis of the recipient for a period of time. For example, such transdermal patches may include a base or matrix layer, e.g., polymeric layer, in which active agent is retained and/or an adhesive layer or may be inherently adhesive. The base or matrix layer may be operably associated with a support or backing. Active agents suitable for transdermal administration may also be delivered by iontophoresis and may take the form of an optionally buffered aqueous solution that includes the active agent. Suitable formulations may include citrate or bis/tris buffer (pH 6) or ethanol/water and contain a suitable amount of active ingredient.

Embodiments may also include administration of active agent via a biodegradable implant active agent delivery device. Such may be accomplished by employing syringes or the cannula 6 insertion syringe to deposit such a biodegradable delivery device under the skin of a subject. The implants degrade completely, so that removal is not necessary.

Embodiments may include employing an electrode to deliver active agent to a subject. For example, an electrode may be used that has a small port at its tip which is connected to a reservoir or pump containing active agent, which may be the same or different than that which contains a therapeutic substance. Such may be delivered via separate lumen of tubing 2 or otherwise. Such an electrode may be included as part of cannula 6 and/or securement element 4. For example, active agent may be contained within the pump and delivered via tubing 2 or other tubing. The active agent delivery electrode may be implanted using any suitable technique such as surgical cut down, laparoscopy, endoscopy, percutaneous procedure, and the like. In certain embodiments a reservoir or pump may also be implanted in the subject's body. The active agent delivery electrode, or other analogous device, may be controllable such that the amount of active agent delivered, the rate at which the active agent may be delivered, and the time period over which the active agent may be delivered, etc., may be controllable and may be adjusted, e.g., by a user and/or healthcare worker, or automatically via suitable software/hardware, e.g., by a controller of the pump. As described above, at least part of an infusion set may include an active agent. An infusion set may include or incorporate active agent thereof in any suitable manner. At least a portion of the infusion set, e.g., a patient-contacting portion, includes active agent, where in certain embodiments substantially the entire infusion set may include the active agent. Active agent may be immobilized on a surface of the one or more components of an infusion set or may be configured to diffuse away from an infusion set surface.

In certain embodiments, active agent is a coating on at least a portion of the infusion set, e.g., on a surface of tubing 2 and/or element 4 and/or cannula 6 and/or optional needle. In certain embodiments, active agent is incorporate, e.g., embedded, or otherwise integrated into the material of one or more of these components of an infusion set. For example, in certain embodiments securement element 4 and/or cannula 6, e.g., outer and/or inner surfaces of the cannula 6, may include active agent such that the securement element 4 and/or cannula 6 may include a coating thereof such that active agent may be incorporated as a thin coating positioned about a surface of the securement element 4 and/or cannula 6. The amount of active agent to be included may be readily controlled by applying multiple thin coats thereof, e.g., and allowing it to dry between coats.

The thickness of a coating will be minimal so as not to appreciably increase the thickness of the coating-containing component. In many embodiments, the thickness is substantially uniform and the active agent is substantially homogenous throughout the area including it.

Alternatively or in addition to a coating, an active agent may be incorporated within the material of an infusion set, e.g., incorporated within the material of tubing 2 and/or patch 4 and/or cannula 6 and/or optional needle, in most instances resulting in active agent that is dispersed evenly throughout the component(s) of the infusion sets (substantially homogeneously).

Embodiments include infusion sets that have the ability to emit or diffuse active agent at a controllable rate, e.g., may include a controlled release, such as a time release, formulation. For example, an infusion set may include a formulation that is designed to release active agent gradually over time, e.g., over about a period of time commensurate with a period of time in which an infusion set is transcutaneously positioned in a patient. A controlled release formulation may employ a polymer or other non active agent material to control the release of the active agent. The active agent release rate may be slowed by diffusion through the polymer, or the active agent may be released as the polymer degrades or disintegrates in the body.

The active agent may be added to the infusion set during fabrication of an infusion set and/or may be applied to an infusion set after it has been fabricated. For example, a coating containing active agent thereof may be applied to an infusion set after it has been fabricated.

Active agent may be applied to an infusion set by any of a variety of methods, e.g., by spraying the active agent onto the infusion set or by dipping the infusion set into the active agent, by coating the active agent with a slotted die, or otherwise immersing or flooding an infusion set with the active agent.

The amount of active agent included in an infusion set may vary depending on a variety of factors such as the particular active agent used, the particulars of the infusion set, etc. In any event, an effective amount of active agent used—an amount sufficient to provide the requisite result, e.g., antibacterial, anti-scarring, and the like, for the desired period of time.

The subject infusion sets may be used with an analyte monitoring system using a sensor at least a portion of which is positioned beneath the skin of the user for the in vivo determination of a concentration of an analyte such as, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, warfarin, and the like, in a body fluid. The sensor may be, for example, subcutaneously positioned in a patient for the continuous or periodic monitoring an analyte in a patient's interstitial fluid. This may be used to infer the glucose level in the patient's bloodstream. Sensors for insertion into a vein, artery, or other portion of the body containing fluid, may also be used. A sensor may be configured for monitoring the level of the analyte over a time period which may range from hours, days, weeks, or longer. For example, a continuous glucose sensing system may be used with an insulin delivery pump that includes an active-agent containing infusion set. At least some components of a glucose sensing system may be integrated with an insulin pump of the subject invention, e.g., as described in U.S. Patent Application Ser. No. 60/664,215, and elsewhere.

Figure 3:
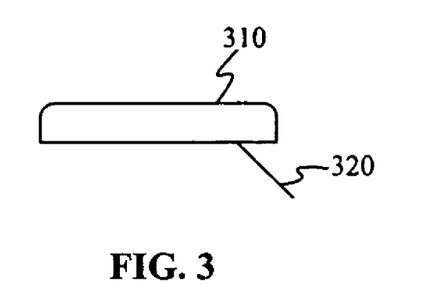
FIG. 3 shows an on-body infusion device directed coupled to a cannula in accordance with one embodiment.

FIG. 3 shows an on-body infusion device directed coupled to a cannula in accordance with one embodiment. Referring to FIG. 3, in one embodiment, a patch pump type infusion device 310 is provided with a cannula 320 directed coupled thereto. As can be seen from the figure, cannula 320 is directly coupled to on-body infusion device 310 without the use of any infusion tubing. In one embodiment, infusion device 310 includes control mechanism to control the infusion of the therapeutic substance such as insulin stored, for example, in a reservoir (not shown) in infusion device 310 to a patient via cannula 320.

Figure 4:
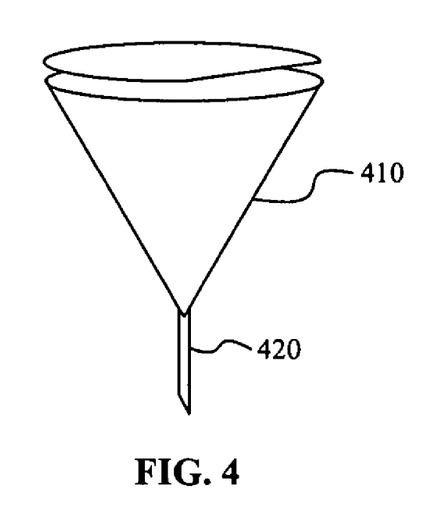
FIG. 4 shows a refillable infusion device directly coupled to a cannula in accordance with one embodiment.

FIG. 4 shows a refillable infusion device directly coupled to a cannula in accordance with one embodiment. As shown in the Figure, cannula 420 is coupled to insulin storage device 410 (which may include an infusion device or a subcomponent thereof) for delivering a therapeutic substance to a patient. Cannula 420 is placed under the patient's skin and is configured to deliver the therapeutic substance such as insulin to the patient. In this embodiment, insulin storage device 410 is configured to receive a predetermined amount of the therapeutic substance to store and subsequently infuse to a patient, using a syringe, for example. In this manner, insulin storage device 410 may be configured to receive insulin through a self-sealing membrane or any other type of suitable non-porous membrane, after the placement of cannula 420 under the patient's skin.

Figure 5A:
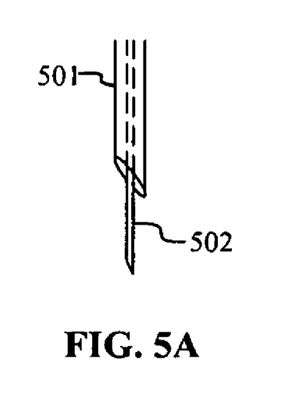
FIGS. 5A-5B show a dual cannula infusion set configuration in accordance with still further embodiments of the present invention.
Figure 5B:
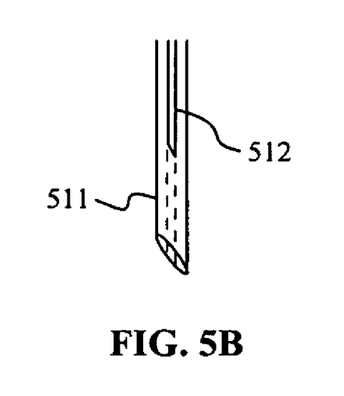

FIGS. 5A-5B show a dual cannula infusion set configurations in accordance with still further embodiments of the present invention. Referring to FIG. 5A, an inner cannula 502 is shown to be substantially surrounded by an outer cannula 501, where during the initial placement of the infusion set, both the inner cannula 502 and the outer cannula 501 are substantially simultaneously placed under the skin of the patient. Moreover, as can be seen from FIG. 5A, the inner cannula 502 is placed at a greater depth under the patient's skin as compared to the relative placement of the outer cannula 501. In this manner, after a predetermined time period of usage has elapsed (for example, about 3 days), the inner cannula 502 in one embodiment is withdrawn or retracted from the patient, while retaining the outer cannula 501 in the original place under the skin of the patient.

Accordingly, the usage time may be extended beyond the typical 3 day period by using outer cannula 501 for insulin infusion, for example, subsequent to the first 3 days. In this manner, the extended usage of the infusion set may be desirable further when the infusion system including the infusion device and the infusion set is used in conjunction with a 5 day or 7 day continuous monitoring system such as a continuous glucose monitoring system.

Referring back to FIG. 5B, in a further embodiment, the dual cannula infusion set configuration as shown may include an outer cannula 511 and a separate inner cannula 512, where the outer cannula 511 is placed at a greater depth under the patient's skin as compared to the relative placement of the inner cannula 512. In this embodiment, as compared to the embodiment shown in FIG. 5A, the outer cannula 511 is first placed under the skin during the initial infusion period of for example, 3 days. Thereafter, prior to the removal or withdrawal of the outer cannula 511, the inner cannula 512 inserted or positioned within the outer cannula 511 and under the patient's skin, though at a less depth as compared to the placement of the outer cannula 511. Thereafter, with the removal or withdrawal of the outer cannula after the first three days of usage, the inner cannula 512 may be configured to continuously deliver the therapeutic substance such as insulin. In this manner, with a single skin piercing (of the outer cannula 511 placement) and thereby minimizing skin trauma as well as associated pain, the infusion set may be used for extended time period such as 5 days or 7 days.

In certain embodiments, in addition to, or instead of, an infusion set and/or other associated structure including an active agent, at least a portion of a continuous analyte monitoring system may include active agent. For example, a portion of an analyte sensor, transmitter mount, and the like, may include an antimicrobial agent and/or anti-scarring agent.

The analyte sensors and analyte monitoring systems of the present invention may be utilized under a variety of conditions. The particular configuration of a sensor and other units used in an analyte monitoring system may depend on the use for which the sensor and system are intended and the conditions under which the sensor and system will operate. As noted above, embodiments include a sensor configured for implantation into a patient or user. The term "implantation" is meant broadly to include wholly implantable sensors and sensors in which only a portion of which is implantable under the skin and a portion of which resides above the skin, e.g., for contact to a transmitter, receiver, transceiver, processor, etc. For example, implantation of the sensor may be made in the arterial or venous systems for direct testing of analyte levels in blood. Alternatively, a sensor may be implanted in the interstitial tissue for determining the analyte level in interstitial fluid. This level may be correlated and/or converted to analyte levels in blood or other fluids. The site and depth of implantation may affect the particular shape, components, and configuration of the sensor. Subcutaneous implantation may be desired, in some cases, to limit the depth of implantation of the sensor. Sensors may also be implanted in other regions of the body to determine analyte levels in other fluids. Examples of suitable sensors and sensor systems for use in the subject invention are described, for example, in U.S. Pat. Nos. 6,175,752, 6,284,478, 6,134,461, and elsewhere.

Figure 6:
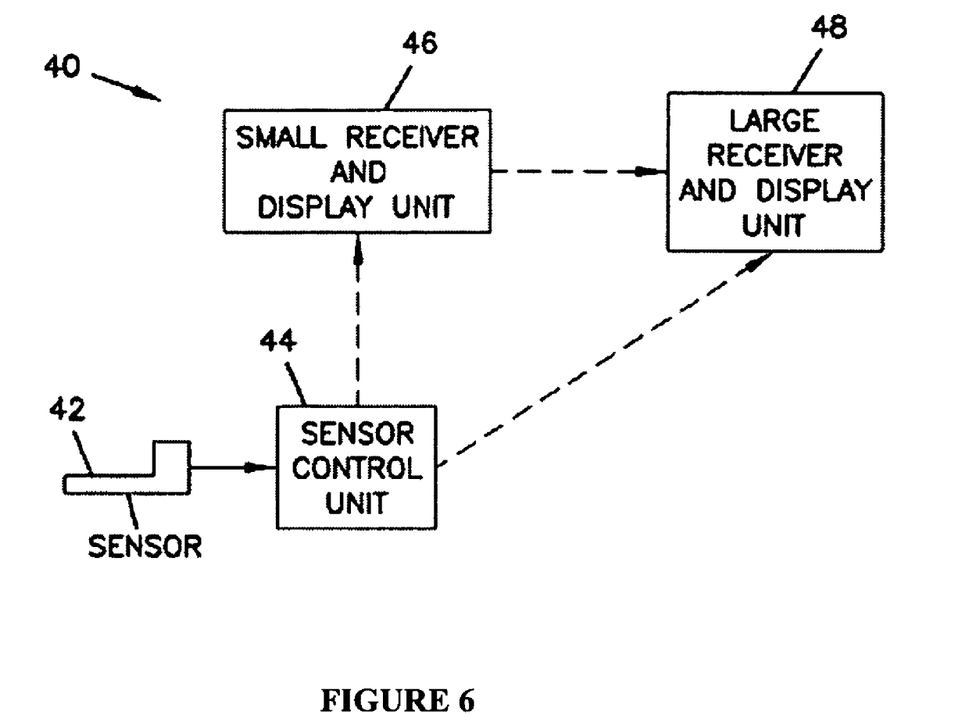
FIG. 6 shows a block diagram of an exemplary embodiment of an analyte monitoring system using an implantable analyte sensor, according to the invention.

An exemplary embodiment of an analyte monitoring system 40 for use with a medication delivery device 10 is illustrated in block diagram form in FIG. 6. The analyte monitoring system 40 includes, at minimum, a sensor 42, a portion of the sensor which is configured for implantation (e.g., subcutaneous, venous, or arterial implantation) into a patient, and a sensor control unit 44. Sensor 42 is coupleable to sensor control unit 44 which is typically attachable to the skin of a patient. Sensor control unit 44 operates sensor 42, including, for example, providing a voltage across the electrodes of the sensor 42 and collecting signals from the sensor 42. Sensor control unit 44 may evaluate the signals from sensor 42 and/or transmit the signals to one or more optional receiver/display units 46, 48 for evaluation. Sensor control unit 44 and/or receiver/display units 46, 48 may display or otherwise communicate the current level of the analyte. Control unit 44 and one or more optional receiver/display units 46, 48 may be combined in a single unit or may be separate. Furthermore, sensor control unit 44 and/or the receiver/display units 46, 48 may indicate to the patient, via, for example, an audible, visual, or other sensory-stimulating alarm, when the level of the analyte is at or near a threshold level. In some embodiments, an electrical shock may be delivered to the patient as a warning through one of the electrodes or the optional temperature probe of the sensor. For example, if glucose is monitored then an alarm may be used to alert the patient to a hypoglycemic or hyperglycemic glucose level and/or to impending hypoglycemia or hyperglycemia.

Sensor 42 includes at least one working electrode and a substrate. Sensor 42 may also include at least one counter electrode (or counter/reference electrode) and/or at least one reference electrode. The counter electrode and/or reference electrode may be formed on the substrate or may be separate units. For example, the counter electrode and/or reference electrode may be formed on a second substrate which is also implantable in the patient or, for some embodiments of the sensors the counter electrode and/or reference electrode may be placed on the skin of the patient with the working electrode or electrodes being implanted into the patient. The use of an on-the-skin counter and/or reference electrode with an implantable working electrode is described in, e.g., U.S. Pat. No. 5,593,852.

On-skin sensor control unit 44 may optionally contain a transmitter or transceiver (not shown) for transmitting the sensor signals or processed data from a processing circuit to a receiver (or transceiver)/display unit 46, 48; to pump 8, a data storage unit (not shown) for temporarily or permanently storing data; a reference voltage generator (not shown) for providing a reference voltage for comparison with sensor-generated signals; and/or a watchdog circuit that monitors the operation of the electronic components in the on-skin sensor control unit.

One or more receiver/display units 46, 48 may be provided with the analyte monitoring device 40 for easy access to the data generated by the sensor 42 and may, in some embodiments, process the signals from the on-skin sensor control unit 44 to determine the concentration or level of analyte in the subcutaneous tissue. Small receiver/display units 46 may be carried by the patient. The receiver may be a transceiver. Receivers may be palm-sized and/or may be adapted to fit on a belt or within a bag or purse that the patient carries.

The receiver/display units 46, 48 typically include a receiver to receive data from the on-skin sensor control unit 44, an analyzer to evaluate the data, a display to provide information to the patient, and an optional alarm system to warn the patient when a condition arises. The receiver/display units 46, 48 may also optionally include a data storage device, a transmitter, and/or an input device such as a keypad or keyboard. The input device 162 may allow numeric or alpha-numeric input. The input device 162 may also include buttons, keys, or the like which initiate functions of and/or provide input to the analyte monitoring device 40. Such functions may include initiating a data transfer, inputting calibration data, and/or indicating events to activate storage of data representative of the event.

The receiver/display units 46,48 may also include other components such as a power supply (e.g., a battery and/or a power supply that can receive power from a wall outlet), a watchdog circuit, a bias current generator, and an oscillator. These additional components are similar to those described above for the on-skin sensor control unit 44. The receiver/display units 46, 48 may also include a number of optional items. One item is a data storage unit which may be desirable to store data for use if the analyzer is configured to determine trends in the analyte level. The data storage unit may also be useful to store data that may be downloaded to another receiver/display unit or to a computer or other data storage device in a patient's home, at a doctor's office, etc. for evaluation of trends in analyte levels.

Sensor 42 and the electronic components within the on-skin sensor control unit 44 are coupled via conductive contacts. The one or more working electrodes, counter electrode (or counter/reference electrode), optional reference electrode are attached to individual conductive contacts. The conductive contacts may be provided on the interior of the on-skin sensor control unit 44. Other embodiments of the on-skin sensor control unit 44 have the conductive contacts disposed on the exterior thereof. The placement of the conductive contacts is such that they are in contact with contact pads on the sensor when the sensor is properly positioned within the on-skin sensor control unit 44.

In certain embodiments, electrical contacts may be eliminated between the sensor 42 and the on-skin sensor control unit 44. Power may be transmitted to the sensor via inductive coupling, using, for example, closely space antennas (e.g., facing coils) (not shown) on the sensor and the on-skin sensor control unit.

A sensor may be adapted to be a replaceable component in an in vivo analyte monitor, and particularly in an implantable analyte monitor. In many embodiments, the sensor is capable of operation over a period of days or more, e.g., a period of operation may be at least about one day, e.g., at least about three days, e.g., at least about one week or more. The sensor may then be removed and replaced with a new sensor.

As noted herein, analyte monitoring system 40 may be coupled with pump 10 so that analyte, e.g., glucose, information is automatically sent to the pump, where such information may be used to determine the appropriate amount of insulin to deliver to the patient, where in certain embodiments system 40 and device 10 may be integrated to provide an integrated infusion device and monitoring system.

For example, the subject invention also includes sensor-based medication delivery systems. The system may provide a medication such as insulin to counteract the high or low level of the analyte, e.g., glucose, in response to the signals from one or more sensors. Alternatively, the system may monitor the glucose concentration to ensure that the insulin remains within a desired therapeutic range. An insulin delivery system may include one or more (e.g., two or more) glucose sensors, an on-skin sensor control unit, a receiver/display unit, a data storage and controller module, and an insulin administration system, wherein the sensor, insulin pump device, or both, include active agent as described herein. In some cases, the receiver/display unit, data storage and controller module, and insulin administration system may be integrated in a single unit. The sensor-based insulin delivery system uses data from the one or more glucose sensors to provide necessary input for a control algorithm/mechanism in the data storage and controller module to control and adjust the administration of insulin.

Finally, kits for use in practicing the subject invention are also provided. The subject kits may include an infusion set that includes an active agent. For example, a kit may include one or more infusion sets as described herein, and/or other structure that includes an active agent to be used with the infusion set. In certain embodiments, a kit may include a therapeutic agent delivery device that includes such an infusion set and a housing for containing a therapeutic substance and controlling the delivery of the therapeutic substance to a patient. In many embodiments, an insulin pump is included in a kit, the insulin pump including an infusion set having active agent. Embodiments may also include an analyte sensor (e.g., glucose sensor) such as a continuous analyte sensor and/or sensor insertion device and/or transmitter and/or receiver.

In addition to one or more active agent-including infusion sets, the subject kits may also include written instructions for using the infusion sets. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

In many embodiments of the subject kits, the components of the kit are packaged in a kit containment element to make a single, easily handled unit, where the kit containment element, e.g., box or analogous structure, may or may not be an airtight container, e.g., to further preserve the contents of the kit until use.

It is evident from the above results and discussion that the above-described invention provides active agent-including medication infusion devices such as antimicrobial and/or anti-scarring glucose pumps. The above-described invention provides a number of advantages—some of which are described above and which include, but are not limited to, reduced risk of infection and/or scarring and prolonged use. As such, the subject invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A system for delivering a therapeutic fluid to a patient, the system comprising:

an infusion set comprising at least one transcutaneous cannula configured for delivering the therapeutic fluid to within the patient;

a securement element for securing the infusion set to the patient;

an implantable sensor for monitoring an analyte wherein the sensor is physically associated with the securement element;

an active agent comprising at least one of an antimicrobial agent or an anti-scarring agent or both an antimicrobial agent and an anti-scarring agent; and a non-active agent for controllably releasing the active agent over a predetermined time period.

2. The system of claim 1, wherein the active agent is provided on at least a portion of the infusion set.

3. The system of claim 1, wherein the active agent is applied by one or more of spraying, dipping or coating the at least one cannula.

4. The system of claim 1, wherein the active agent is provided on the securement element.

5. The system of claim 1, wherein the infusion set further comprises an insertion element for inserting the at least one cannula into the patient.

6. The system of claim 5, wherein the active agent is provided on the insertion element.

7. The system of claim 1, wherein the infusion set further comprises tubing configured for fluid communication between a source of the therapeutic fluid and the at least one cannula.

8. The system of claim 7, wherein the active agent is provided on the tubing.

9. The system of claim 1, wherein the active agent is provided on the implantable sensor.

10. The system of claim 1, wherein the active agent is a coating.

11. The system of claim 10, wherein the coating comprises multiple coats of the active agent.

12. The system of claim 1, wherein the active agent is integrated into the material of the infusion set.

13. The system of claim 1, wherein the antimicrobial agent comprises at least one of penicillin, mupirocin, erthromycin, polymyxin, silver sulfadiazine, cephalosporins, bacitracin, tetracycline, doxycycline, gentamycin, quinolines, neomycin, clindamycin, kanamycin, metronidazole, iodine, Povidine-iodine, benzalkonium chloride, benzoic acid, chlorhexidine, nitrofurazone, benzoyl peroxide, hydrogen peroxide, hexachlorophene, phenol, resorcinol, and cetylpyridinium chloride, nystatin, ciclopirox, chloroxylenol, triacetin, sulconazole, undecylenic acid, tolnaftate, miconizole, clotrimazole, oxiconazole, griseofulvin, econazole, ketoconozole, and amphotericin B, acyclovir, ribarivin, interferons, nitrofurazone, iodine, silver nitrate, silver sulfadiazine, zinc oxide, or combinations thereof.

14. The system of claim 1, wherein the therapeutic fluid comprises insulin and the sensor comprises a glucose sensor.

15. The system of claim 14, further comprising an insulin delivery device wherein the system is configured to communicate glucose information from the glucose sensor to the insulin delivery device.

16. The system of claim 15, wherein the system is configured to automatically communicate the glucose information from the glucose sensor to the insulin delivery device.

17. The system of claim 15, wherein the insulin delivery device is configured to determine an amount of insulin to be delivered based on the glucose information from the glucose sensor.

18. The system of claim 1, wherein the non-active agent comprises a polymer.

19. The system of claim 18, wherein the polymer is configured to at least partially degrade or disintegrate over the predetermined time period.

20. The system of claim 1, wherein the non-active agent provides a diffusion layer between the patient and the at least one cannula.

21. The system of claim 1, wherein the predetermined time period comprises at least approximately three days.

22. The system of claim 1, wherein the securement element comprises a skin-contacting surface substantially transverse to the at least one cannula.

23. The system of claim 22, wherein the skin-contacting surface of the securement element is substantially transverse to the implantable sensor.

24. The system of claim 22, wherein the skin-contacting surface of the securement element provides the active agent.

25. The system of claim 22, wherein the skin-contacting surface comprises an adhesive.

26. The system of claim 1, wherein the at least one transcutaneous cannula comprises an inner cannula and an outer cannula wherein a portion of the inner cannula is disposed within the outer cannula.

27. The system of claim 26, wherein the inner cannula and the outer cannula are configured to be simultaneously inserted through a skin layer of the patient.

28. The system of claim 26, wherein the inner cannula and the outer cannula are configured to be separately inserted through a skin layer of the patient.

29. The system of claim 26, wherein the inner cannula and the outer cannula are configured to be positioned at a respective first location and a second location under the skin layer.

30. The system of claim 29, wherein the first location and the second location are different.

31. The system of claim 30, wherein the first location is at a greater depth than the second location.

32. The system of claim 30, wherein the second location is at a greater depth than the first location.

33. The system of claim 26, wherein the inner cannula and the outer cannula are configured to be withdrawn from the patient at respective different times.

34. The system of claim 26, wherein the active agent is provided on the outer cannula.

35. The system of claim 26, wherein the active agent is applied to an outer surface of the outer cannula and to an outer surface of the inner cannula excluding the outer surface of the portion of the inner cannula that is disposed within the outer cannula.

* * * * *